(12) United States Patent
Palasis

(10) Patent No.: US 6,398,808 B1
(45) Date of Patent: Jun. 4, 2002

(54) LOCALIZED DELIVERY OF GENETIC INFORMATION FROM BIOSTABLE MATERIALS

(75) Inventor: Maria Palasis, Wellesley, MA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/333,032

(22) Filed: Jun. 15, 1999

(51) Int. Cl.$^7$ .................................................. A61F 2/06
(52) U.S. Cl. ..................................... 623/1.46; 623/1.39
(58) Field of Search ................................ 623/1.39, 1.4, 623/1.42, 1.43–1.48; 424/422–426; 604/890.1, 891.1, 502

(56) References Cited

U.S. PATENT DOCUMENTS

| | | | |
|---|---|---|---|
| 4,304,010 A | * 12/1981 | Mano | 3/1.4 |
| 5,156,844 A | 10/1992 | Aebischer et al. | 424/424 |
| 5,344,654 A | * 9/1994 | Rueger et al. | 424/423 |
| 5,512,291 A | * 4/1996 | Li | 424/443 |
| 5,549,664 A | * 8/1996 | Hirata et al. | 623/1 |
| 5,591,227 A | * 1/1997 | Dinh et al. | 623/1 |
| 5,595,621 A | * 1/1997 | Light et al. | 156/80 |
| 5,624,674 A | * 4/1997 | Seare, Jr. | 424/400 |
| 5,660,854 A | 8/1997 | Haynes et al. | 424/450 |
| 5,674,192 A | 10/1997 | Sahatjian et al. | 604/28 |
| 5,713,949 A | * 2/1998 | Jayaraman | 623/1 |
| 5,788,979 A | * 8/1998 | Alt et al. | 424/426 |
| 5,824,056 A | * 10/1998 | Rosenberg | 623/1 |
| 5,843,172 A | 12/1998 | Yan | |
| 5,847,012 A | * 12/1998 | Shalaby et al. | 521/61 |
| 5,865,796 A | 2/1999 | McCabe | 604/71 |
| 5,876,452 A | * 3/1999 | Athanasiou et al. | 623/16 |
| 5,914,125 A | * 6/1999 | Andrews et al. | 424/443 |
| 6,013,099 A | * 1/2000 | Dinh et al. | 623/1 |
| 6,153,292 A | * 11/2000 | Bell et al. | 428/305.5 |
| 6,241,774 B1 | * 6/2001 | Shimizu | 623/23.64 |

FOREIGN PATENT DOCUMENTS

EP 0 835 894 4/1998

OTHER PUBLICATIONS

H.W. Kang, Y. Tabata, and Y. Ikada, *Preparation of Porous Gelatin Hydrogels for Tissue Engineering*, Controlled Release Society, Inc./Proceed Int'l. Symp. Control. Rel. Bioact. Mater., 25 (1998) pp. 164–165.
Jong, et al., *Journal of Controlled Release*, 47 (1997) 123–134.
Kang, et al., *Proceed. Int'l. Symp. Control. Rel. Bioact. Mater.*, 25 (1998) 164–165.
Gemeinhart, et al., *Proceed Int'l. Symp Control. Rel. Bioact. Mater.*, 25 (1998) 360–361.
Rajasubramanian, et al., *ASAIO Journal*, (1994), 40: M584–M589.
Gao, et al., "Intravascular Local Gene Transfer Mediated by Protein–Coated Metallic Stent," Abstract:1669.
Chen, et al., *J. Biomed. Mater. Res.*, 44:53–62 (1999).
Webber, et al., *J. Biomed. Mater. Res.*, 41:18–29 (1998).
Goodwin, et al., *J. Biomed. Mater. Res.*, 40:204–213 (1998).

* cited by examiner

*Primary Examiner*—Sharon Kennedy
(74) *Attorney, Agent, or Firm*—Kenyon & Kenyon

(57) ABSTRACT

Medical devices and systems for the localized delivery of genetic information to a target location within a mammalian body. In one embodiment, the system comprises a medical device insertable into the body and a biostable coating over at least part of the medical device. Genetic information is incorporated into the biostable coating before the medical device is placed into the body, and is released from the biostable coating at a target location within the body. The invention also includes methods for the localized delivery of genetic information to target locations within a mammalian body using the medical devices and systems of the invention.

56 Claims, 4 Drawing Sheets

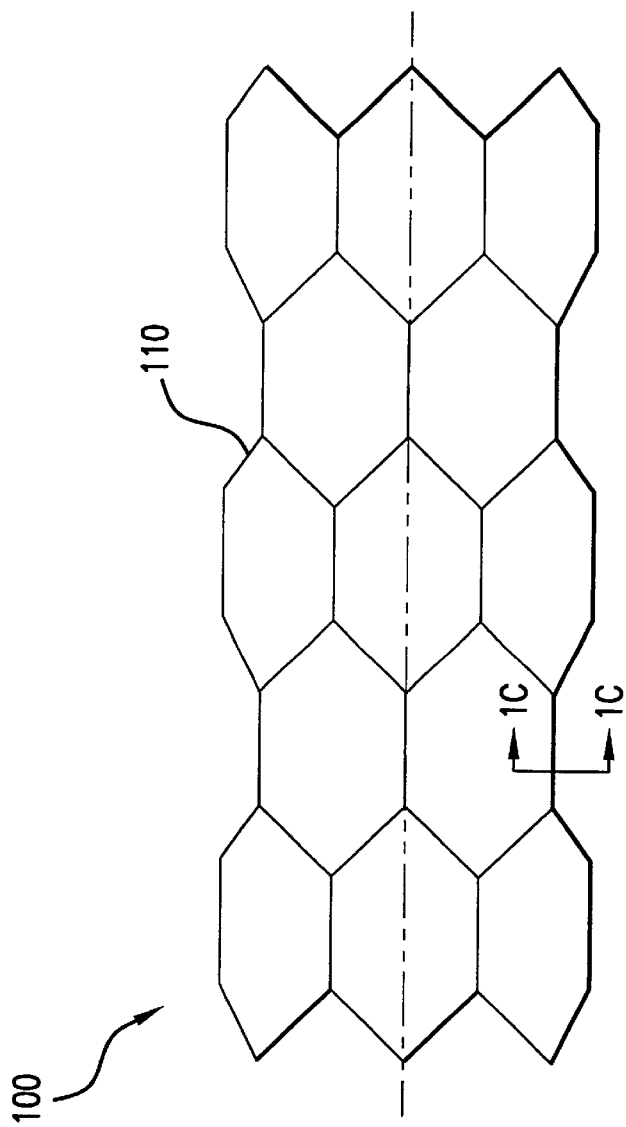
FIG. 1A
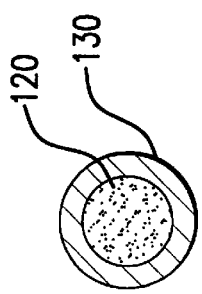
FIG. 1C
FIG. 1B

LOCALIZED DELIVERY OF GENETIC INFORMATION FROM BIOSTABLE MATERIALS

FIELD OF THE INVENTION

The present invention relates to the localized delivery of genetic information to target locations within the mammalian body, and more particularly to the delivery of genetic information from biostable materials coated onto medical devices.

BACKGROUND OF THE INVENTION

The treatment of disease such as vascular disease by local pharmacotherapy presents a means of delivering therapeutic drug doses to target tissues while minimizing systemic side effects. Recently, for example, the local delivery of gene constructs to effect vascular response has gained increased interest. Gene transfection of vascular smooth muscle cells in vivo, however, is often difficult because of the low transfer efficiency attributed in part to inefficient local delivery devices and to the barrier properties of the vessel wall.

As an example of localized delivery of therapeutic agents, in vivo adenoviral gene transfer has been accomplished with the use of site-specific delivery catheters. Because genetic materials are typically in the form of large molecules, however, it has been difficult to engineer biostable delivery materials that can hold the genetic materials during delivery within the body and then release the genetic materials upon reaching a target location. Rather, such delivery is accomplished by incorporating the genetic information into a biodegradable medical device or coating, whereby the genetic information is released as the biodegradable material disintegrates while in the body. The use of biodegradable materials within the body, however, often results in adverse interactions with tissue and the resultant inflammation thereof. Further, biodegradable materials are generally characterized by a short shelf-life because they typically degrade upon exposure to the ambient atmosphere.

SUMMARY OF THE INVENTION

In one aspect, the present invention relates to a system for the localized delivery of genetic information to a target location within a mammalian body. In one embodiment, the system comprises a medical device insertable into the body and a biostable coating over at least part of the medical device. Genetic information is incorporated into the biostable coating before the medical device is placed into the body, and is released from the biostable coating at a target location within the body.

In another aspect, the present invention relates to method for the localized delivery of genetic information to a target location within a mammalian body. In one embodiment, the method includes the steps of providing a medical device insertable into the body, coating at least a portion of the medical device with a biostable material, incorporating the genetic information into the biostable material, and placing the medical device at the target location. The genetic information is released from the biostable material at the target location.

In another aspect, the present invention relates to medical devices at least partially covered with a biostable coating that facilitates the localized delivery of genetic information.

One advantage of the present invention is that it provides biostable coatings for medical devices, and methods of making such coatings, that are suitable for holding and releasing genetic information.

Another advantage of the present invention is that it provides for the localized delivery of genetic information from biostable materials, thus avoiding the potential problems of delivery from biodegradable polymers.

Yet another advantage of the present invention is that it provides for the localized delivery of genetic information in a controlled and reproducible manner.

BRIEF DESCRIPTION OF THE DRAWINGS

FIG. 1 shows a medical device coated with a porous coating for the localized delivery of genetic information, in accordance with an embodiment of the invention.

DETAILED DESCRIPTION

Figure 2:
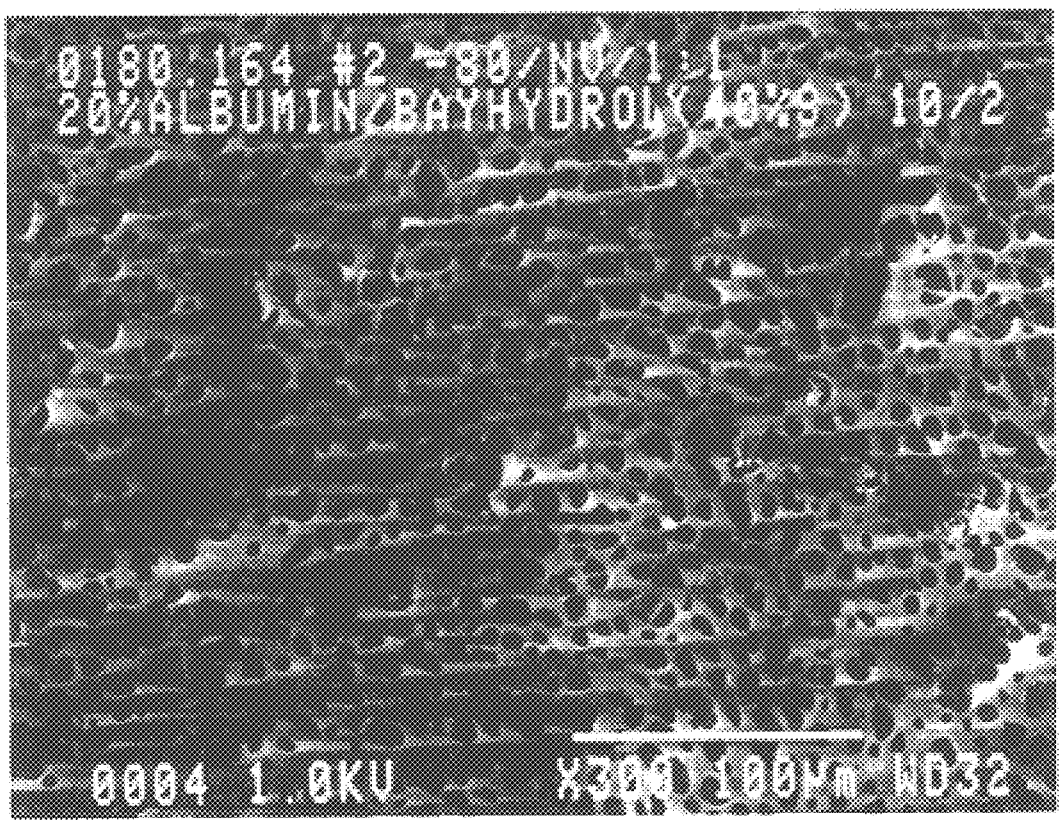
FIG. 2 shows a normal view of a polymer structure having an interconnected pore structure, in accordance with an embodiment of the invention.

The present invention provides for the localized delivery of genetic information to target locations within the body. The delivery systems, methods and medical devices of the invention are novel in that they make use of biostable coating materials to deliver the genetic information to the target locations. As used herein, "biostable materials" refer to those materials that do not undergo significant degradation upon prolonged exposure (i.e., up to six months, a year, or longer) to bodily fluids, tissues, and the like. The biostable coating materials of certain embodiments of the invention are porous polymer materials that are characterized by interconnected pores of sufficient size to allow for the incorporation therein, and release therefrom, of genetic information.

The biostable, porous polymer materials of the present invention are formed by methods not previously used to form coatings on medical devices and are thus characterized by novel coating properties. The porous polymer materials are preferably characterized by an average pore diameter of at least about 5 microns, more preferably at least about 8 microns, and more preferably at least about 10 microns.

In one embodiment, polymer coatings containing large interconnected pores are formed by a freeze-dried process in which a medical device is coated with an aqueous polymer solution that is rapidly frozen and then lyophilized. During lyophilization, ice within the coating sublimes from the coating to leave an interconnected pore structure. The size of the resulting pores is controlled by processing parameters such as the freezing rate during the freeze-drying process, and the water content of the pre-coating formulation. The result of the freeze-drying process is a medical device coated with a biostable polymer coating characterized by an interconnected pore structure that is capable of having genetic information incorporated therein.

Suitable polymers for use in embodiments wherein a porous structure is obtained by freeze-drying include any suitable biostable polymer, such as polyurethanes (including polyurethane dispersions), ethylene vinylacetate polymers, hydrogels such as crosslinked gelatin, dextran, polycarboxylic acids, cellulosic polymers, gelatin, polyvinylpyrrolidone, maleic anhydride polymers, acrylic latex dispersions, polyamides, polyvinyl alcohols, polyethylene oxides, glycosaminoglycans, polysaccharides, polyesters, polyacrylamides, polyethers, and blends and copolymers thereof.

In accordance with the invention, the genetic information delivered by polymer coatings that are freeze-dried is incorporated into the polymer either during or after coating formation. In the former case, the genetic information is, for example, placed into solution with an aqueous dispersion of polymer (or alternatively, an emulsion or dispersion of a water-based solution of genetic information is placed into solution with a polymer in an organic solvent such as methylene chloride), which is thereafter applied to the medical device as a coating. In the latter case, the genetic information is applied to the coating by absorption, such as by dipping. In this situation, the coating preferably consists of a blend of a charged polymer and a neutral flexible polymer, wherein the charged polymer interacts with oppositely charged genetic information and the flexible polymer provides desired-mechanical properties required for a device coating. The charged polymer allows for the rapid loading of large quantities of genetic information, and results in a delivery rate that is dependent on the size of the pores as well as the rate of dissociation between the genetic information and the charged polymer.

In certain other embodiments, polymer coatings containing large interconnected pores are formed by incorporating water-soluble particles into a polymer coating during fabrication thereof. For example, water-soluble particles are dispersed in a solution of dissolved polymer such that a stable dispersion is formed. This solution is coated onto a medical device and dried. The coating is thereafter exposed to water, thus allowing the water-soluble particles to dissolve and diffuse out of the coating. The result is a polymer coating characterized by a large, interconnected pore structure, the size of which depends on factors such as the molecular weight of the water-soluble particles and/or the weight ratio of the water-soluble particles to the polymer. Genetic information is then loaded into the coating by any suitable means, such as by dipping or spraying. As an alternative to loading the genetic information after the diffusion of water-soluble particles out of the coating, the genetic information is incorporated into the coating during fabrication thereof. In this latter case, both the genetic information and the water-soluble particles exist in the coating until released upon delivery into the body, and the water-soluble particles are either inert or bioactive additives.

The medical devices onto which the biostable coatings of the invention are placed include any suitable device including implantable devices such as catheters, stents, needle injection devices, blood clot filters, vascular grafts, stent grafts, biliary stents, colonic stents, bronchial/pulmonary stents, esophageal stents, ureteral stents, aneurysm filling coils and other coiled coil devices, trans myocardial revascularization ("TMR") devices, percutaneous myocardial revascularization ("PMR") devices etc., as are known in the art, as well as devices such as hypodermic needles, soft tissue clips, holding devices, muscle implants and other types of medically useful devices. Such devices are delivered to and/or implanted at target locations by known techniques. Delivery is optionally performed with a sheath that covers the coated medical device to help inhibit the release of the genetic information prior to reaching a target location.

FIG. 1 shows a coated vascular stent 100 as an example of a coated medical device of the present invention. The coated stent 100 includes a stent structure 110 having struts 120 of any suitable metallic or polymeric material, as is known in the art. At least part of the stent structure 110 includes a biostable coating 130 capable of incorporating and releasing genetic information.

Useful therapeutic applications to which the present invention can be applied include, without limitation, methods for treating, ameliorating, reducing and/or inhibiting any lumen or tissue injury, including those that result in denuding the interior wall of a lumen, namely its endothelial lining, including the lining of a blood vessel, urethra, ureter, lung, colon, urethra, biliary tree, esophagus, prostate, fallopian tubes, uterus, vascular graft, or the like. Such injuries result from disease, as in the case of atherosclerosis or urethral hyperplasia (strictures), and/or from mechanical injury from, for example, deployment of an endolumenal stent or a catheter-based device, including balloon angioplasty and related devices.

Vascular therapies that benefit using the methods disclosed herein include, without limitation, cardiomyopathies, cardiac and cerebral strokes, embolisms, aneurysms, atherosclerosis, and peripheral and cardiac ischemias. Delivery of genes encoding proteins competent to induce collateral blood vessel formation can be used to advantage in treating these disorders. Delivery of genes encoding proteins competent to interfere with neointimal (smooth muscle) cell proliferation also is particularly useful in treating restenosis.

Non-vascular therapies that benefit using the methods disclosed herein include biliary, uretal strictures, and urogential applications including therapies for incontinence, kidney stones and the like. Here devices typically are implanted for a prescribed period of time and local delivery of genetic agents competent to induce an antibacterial, anti-inflammatory, or anti-encrustation effect are advantageous. In other applications, the delivery of genetic anti-inflammatory agents is used to treat prostatitis, interstitial cystitis and other urogenital inflammatory disorders. Genetic antiproliferative agents can also be used in endometriosis therapies. Still another application is in the delivery of genetic anticancer agents. The methods of the invention can be applied to therapies for bladder, prostate and uterine cancer.

Specific examples of genetic information used in conjunction with the present invention include, for example, nucleic acids (including, for example, recombinant nucleic acids; naked DNA, cDNA, RNA; genomic DNA, cDNA or RNA in a non-infectious vector or in a viral vector which may have attached peptide targeting sequences; antisense nucleic acid (RNA or DNA); and DNA chimeras which include gene sequences and encoding for ferry proteins such as membrane translocating sequences ("MTS") and herpes simplex virus-1 ("VP22")); oligonucleotides; ribozymes; anti-sense genes; DNA compacting agents; and gene/vector systems (i.e., anything that allows for the uptake and expression of nucleic acids).

Examples of therapeutic polynucleotides include anti-sense DNA and RNA; DNA coding for an anti-sense RNA; or DNA coding for tRNA or rRNA to replace defective or deficient endogenous molecules. The polynucleotides of the invention can also code for therapeutic proteins or polypeptides. Included are survival genes which protect against cell death, such as anti-apoptotic Bcl-2 family factors and Akt kinase; anti-proliferative genes such as Fas Ligand, thymidine kinase/ganciclovir, and cell cycle inhibitors such as CDK inhibitors, Rb and E2F. Still other useful factors include those inhibiting restenosis, angiogenic factors such as bFGF, aFGF, VEGF, HIF1, Del1, PlGF, PDGF, VEGF, vascular endothelial growth factor, epidermal growth factor, transforming growth factor α and β, platelet-derived enothelial growth factor, platelet-derived growth factor, tumor necrosis factor α, hepatocyte growth factor, and insulin like growth factor DNA encoding polypeptides including monocyte chemoattractant protein ("MCP-1"), and the family of bone morphogenic proteins ("BMP's"). The known proteins include BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Currently preferred BMP's are any of BMP-2, BMP-3, BMP-4, BMP-5, BMP-6 and BMP-7. These dimeric proteins can be provided as homodimers, heterodimers, or combinations thereof, alone or together with other molecules. Alternatively or, in addition, molecules capable of inducing an upstream or downstream effect of a BMP can be provided. Such molecules include any of the "hedgehog" proteins, or the DNA's encoding them.

The present invention is further described with reference to the following non-limiting examples.

EXAMPLE 1

Formation of Interconnected Pore Structure

Polymer coatings characterized by interconnected pore structures were made by a freeze-dry process, in accordance with the present invention.

An aqueous solution of albumin and bahydrol, an aqueous dispersion of polyurethane, was prepared by mixing 10 wt % albumin and 20 wt % bahydrol in solution. Albumin was used as a substitute for genetic molecules. Stainless steel coupons measuring approximately 1 cm×2 cm were dipped into the solution for about 30 seconds to form coatings over the coupons, and then immediately subjected to low temperature environments (i.e., −20° and −80° C.) to freeze the at least partially-liquid coatings. The coupons were then placed in a lyophilizer to sublimate the frozen water in the coatings.

Figure 3:
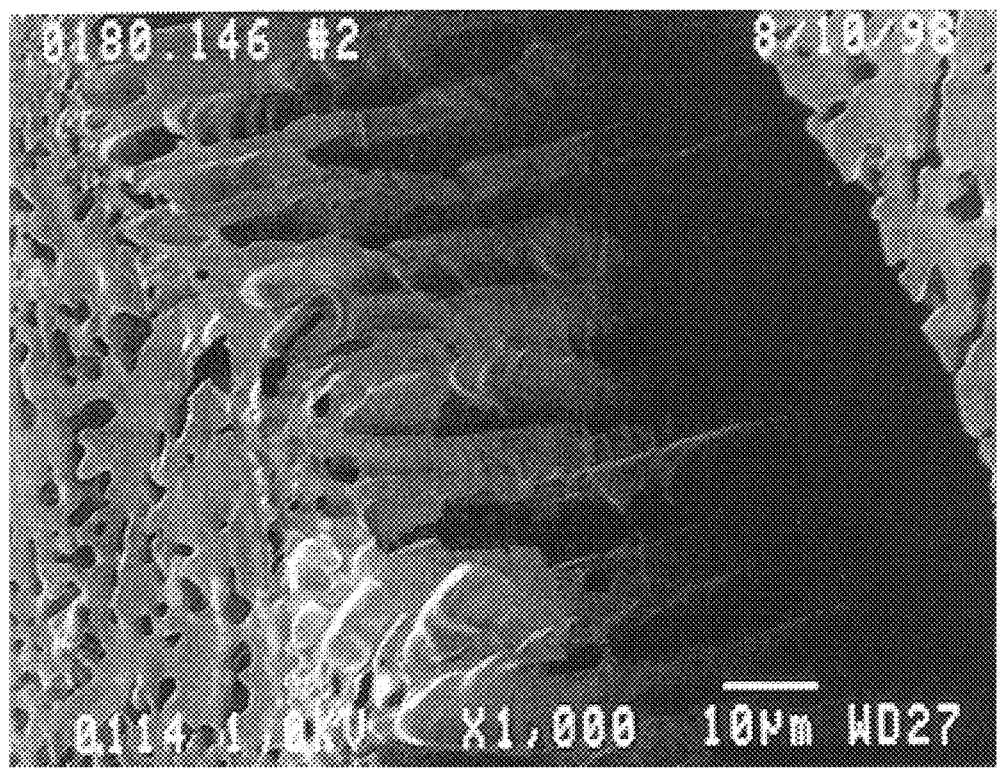
FIG. 3 shows a cross-sectional fracture surface of a polymer structure having an interconnected pore structure, in accordance with an embodiment of the present invention.

The freeze-dry process resulted in polyurethane coatings characterized by a substantially uniform, interconnected pore structures. The final coating composition was about 33% albumin—67% bayhydrol. FIG. 2 is a representative scanning electron micrograph showing the top surface of coatings formed by the process employing the −80° C. freezing temperature. FIG. 3 shows a fracture surface of the coating shown in FIG. 2, thus illustrating the interconnected nature of the pore structure. Generally, the lower freezing temperature (i.e., −80° C.) resulted in smaller pores, and higher pore densities, than the higher freezing temperature (i.e., −20° C.).

EXAMPLE 2

Effect of Drying Time on Pore Structure

Porous polyurethane coatings were formed on coupons in accordance with Example 1. To observe the effects on drying time between dipping the coupons into the polymer solution and placing the coupons into a −80° C. environment, coated coupons were dried in air for time periods of 0, 30, 60 and 300 seconds prior to lyophilization.

The pore sizes resulting from the freeze-dry process were inversely related to drying time. The variation in approximate pore dimensions as a function of drying time are displayed in Table I.

TABLE I

Pore Dimensions as a Function of Drying Time Prior to Freezing.

| Drying Time (s) | Approximate Avg. Pore Diameter (microns) |
|---|---|
| 0 | 9 |
| 30 | 8.5 |
| 60 | 2 |
| 300 | 0 |

EXAMPLE 3

Release of Albumin from Porous Coatings

The coated coupons formed in accordance with Example 1 were placed in phosphate buffered saline for up to 60 minutes to observe the release profiles of albumin from the porous coatings. As a control group, coupons were coated with the polyurethane-albumin solution and allowed to dry in air without freezing. The polymer coatings on the control coupons were thus not characterized by an interconnected porous structure.

Figure 4:
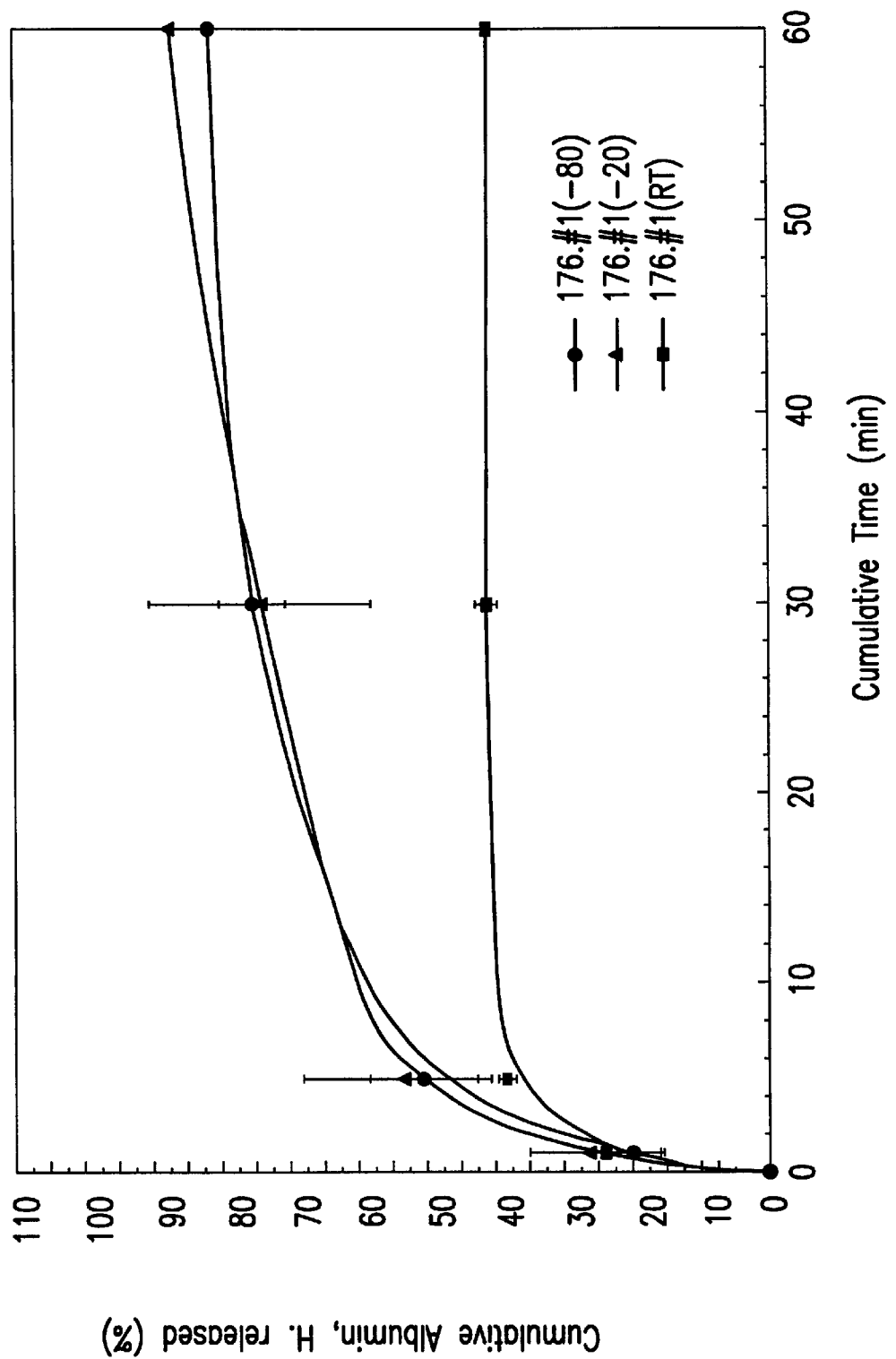
FIG. 4 shows a graph of albumin released from porous polymer coatings in release experiments, in accordance with an embodiment of the present invention.

FIG. 4 shows typical release profiles of tested samples. As can be seen by FIG. 4, there was no statistically significant difference between the release profiles for samples formed in accordance with Example 1 (i.e., samples freeze-dried using −20° C. and −80° C. freezing temperatures). There was, however, a distinct difference between the release from the freeze-dried coupons and those coupons not freeze-dried. Whereas only about 40% of the loaded albumin was released from the coupons not freeze-dried after 60 minutes, about 90% of the loaded albumin was released from the freeze-dried coupons during the same time period. Moreover, whereas the release of albumin from the coupons not freeze-dried was substantially complete after about 10 minutes, the release from the freeze-dried coupons continued throughout the 60-minute test period.

This Example demonstrates that the porous polymer coatings made in accordance with the present invention are well-suited to the efficient release of large molecule materials such as genetic molecules.

The present invention provides for the localized delivery of genetic information to target locations within the body by medical devices coated with biostable coating delivery materials. To facilitate this purpose, the biostable coating materials of certain embodiments of the invention are porous polymer materials that are characterized by interconnected pores of sufficient size to allow for the incorporation therein, and release therefrom, of genetic information. Although the present invention has been described with respect to several exemplary embodiments, there are many other variations of the above-described embodiments which will be apparent to those skilled in the art, even where elements have not explicitly been designated as exemplary. It is understood that these modifications are within the teaching of the present invention, which is to be limited only by the claims appended hereto.

I claim:

1. A system for the localized delivery of genetic information to a target location within a mammalian body, comprising:

a medical device insertable into the body;

an aqueous-based biostable coating over at least part of said device; said biostable coating containing pores formed by freeze-drying said aqueous-based biostable coating and genetic information incorporated into said pores;

wherein the genetic information comprises a material selected from the group consisting of nucleic acids, oligonucleotides, DNA compacting agents, recombinant nucleic acids, and gene/vector systems; which is released from said aqueous-based biostable coating at said target location.

2. The system of claim 1, wherein said aqueous-based biostable coating comprises a material selected from the group consisting of polyurethanes, ethylene vinylacetate polymers, hydrogels, crosslinked gelatin, dextran, cellulose, and blends and copolymers thereof.

3. The system of claim 1, wherein said aqueous-based biostable coating is characterized by an interconnected pore structure.

4. The system of claim 3, wherein said interconnected pore structure has an average pore diameter of at least about 5 microns.

5. The system of claim 3, wherein said interconnected pore structure has an average pore diameter of at least about 10 microns.

6. The system of claim 1, wherein said medical device comprises a stent.

7. The system of claim 1, wherein said medical device comprises a catheter.

8. The system of claim 1, wherein said medical device comprises a needle.

9. The system of claim 1, wherein said medical device comprises a blood filter.

10. The system of claim 1, wherein said medical device comprises a tissue clip.

11. A medical device having a freeze-dried coating comprising an aqueous-based biostable material on at least a portion thereof, said freeze-dried coating further comprising genetic information selected from the group consisting of nucleic acids, oligonucleotides, DNA compacting agents, recombinant nucleic acids, and gene/vector systems.

12. The medical device of claim 11, wherein said aqueous-based biostable material comprises a material selected from the group consisting of polyurethane, ethylene vinylacetate, hydrogels, and blends and copolymers thereof.

13. The medical device of claim 11, further comprising genetic information incorporated into said coating.

14. The medical device of claim 11, wherein said medical device comprises a stent.

15. The medical device of claim 11, wherein said medical device comprises a catheter.

16. The medical device of claim 11, wherein said medical device comprises a needle.

17. The medical device of claim 11, wherein said medical device comprises a blood filter.

18. The medical device of claim 11, wherein said medical device comprises a tissue clip.

19. The medical device of claim 11, wherein said biostable coating has an interconnected pore structure.

20. The medical device of claim 19, wherein said interconnected pore structure has an average pore diameter of at least about 5 microns.

21. The medical device of claim 19, wherein said interconnected pore structure has an average pore diameter of at least about 10 microns.

22. A medical device having a freeze-dried coating on at least a portion of a surface thereof, said coating having genetic information incorporated therein; wherein said freeze-dried biostable coating comprises a charged polymer; which interacts with the oppositely charged genetic information.

23. The medical device of claim 22, wherein said biostable coating comprises a material selected from the group consisting of polyurethane, ethylene vinylacetate, hydrogels, and blends and copolymers thereof.

24. The medical device of claim 22, wherein said genetic information comprises a material selected from the group consisting of nucleic acids, oligonucleotides, DNA compacting agents, recombinant nucleic acids, and gene/vector systems.

25. The medical device of claim 22, wherein said medical device comprises a stent.

26. The medical device of claim 22, wherein said medical device comprises a catheter.

27. The medical device of claim 22, wherein said medical device comprises a needle.

28. The medical device of claim 22, wherein said medical device comprises a blood filter.

29. The medical device of claim 22, wherein said medical device comprises a tissue clip.

30. The medical device of claim 22, wherein said biostable coating has an interconnected pore structure.

31. The medical device of claim 30, wherein said interconnected pore structure has an average pore diameter of at least about 5 microns.

32. The medical device of claim 30, wherein said interconnected pore structure has an average pore diameter of at least about 10 microns.

33. A method of making a medical device having a freeze-dried biostable coating on at least a portion thereof, said coating having genetic information incorporated therein, comprising;
1. placing the genetic information in solution with an aqueous-based dispersion of oppositely charged polymer;
2. coating at least a portion of said medical device with said solution to form a biostable coating;
3. freezing said biostable coating to form a frozen biostable coating; and
4. lyophilizing said frozen biostable coating to create pores in the freeze-dried biostable coating.

34. The method of claim 33, wherein said freeze-dried biostable coating comprises a material selected from the group consisting of polyurethane, ethylene vinylacetate, hydrogels, and blends and copolymers thereof.

35. The method of claim 33, wherein said genetic information comprises a material selected from the group consisting of nucleic acids, oligonucleotides, DNA compacting agents, recombinant nucleic acids, and gene/vector systems.

36. The method of claim 33, wherein said medical device comprises a stent.

37. The method of claim 33, wherein said medical device comprises a catheter.

38. The method of claim 33, wherein said medical device comprises a needle.

39. The method of claim 33, wherein said medical device comprises a blood filter.

40. The method of claim 33, wherein said medical device comprises a tissue clip.

41. The method of claim 33, wherein said biostable coating has an interconnected pore structure.

42. The method of claim 41, wherein said interconnected pore structure has an average pore diameter of at least about 5 microns.

43. The method of claim 41, wherein said interconnected pore structure has an average pore diameter of at least about 10 microns.

44. The method of claim 33, wherein the medical device is dried for a length of time between steps (3) and (4), and wherein the pore diameter depends on said length of time.

45. A method of making a medical device having a freeze-dried biostable coating on at least a portion thereof, said coating having genetic information incorporated therein, comprising;
1. placing the genetic information in solution with an oppositely charged polymer or copolymer to form a biostable solution;
2. coating coating at least a portion of said medical device with said biostable solution;
3. freezing said biostable coating to form a frozen biostable coating; and
4. lyophilizing said frozen biostable coating to create pores in the freeze-dried biostable coating.

46. The method of claim 45, wherein said freeze-dried biostable coating comprises a material selected from the group consisting of polyurethane, ethylene vinylacetate, hydrogels, and blends and copolymers thereof.

47. The method of claim 45, wherein said genetic information comprises a material selected from the group consisting of nucleic acids, oligonucleotides, DNA compacting agents, recombinant nucleic acids, and gene/vector systems.

48. The method of claim 45, wherein said medical device comprises a stent.

49. The method of claim 45, wherein said medical device comprises a catheter.

50. The method of claim 45, wherein said medical device comprises a needle.

51. The method of claim 45, wherein said medical device comprises a blood filter.

52. The method of claim 45, wherein said medical device comprises a tissue clip.

53. The method of claim 45, wherein said biostable coating has an interconnected pore structure.

54. The method of claim 53, wherein said interconnected pore structure has an average pore diameter of at least about 5 microns.

55. The method of claim 53, wherein said interconnected pore structure has an average pore diameter of at least about 10 microns.

56. The method of claim 45, wherein the medical device is dried for a length of time between steps (3) and (4), and wherein the pore diameter depends on said length of time.

* * * * *